United States Patent [19]

Shockman et al.

[11] Patent Number: 4,596,769
[45] Date of Patent: Jun. 24, 1986

[54] MONOCLONAL ANTIBODIES TO PEPTIDOGLYCAN AND METHODS OF PREPARING SAME

[75] Inventors: Gerald D. Shockman, Philadelphia, Pa.; Dianne E. Jackson, Brookline, Mass.; William Wong, Wilmington, Del.

[73] Assignee: Temple University-of the Commonwealth System of Higher Education, Philadelphia, Pa.

[21] Appl. No.: 586,537

[22] Filed: Mar. 5, 1984

[51] Int. Cl.$^4$ .................. G01N 53/00; C12N 5/00; C07K 15/00
[52] U.S. Cl. .................. 435/7; 435/68; 435/240; 435/172.2; 436/536; 436/539; 436/542; 436/548; 436/804; 436/815; 436/825; 436/518; 935/104; 935/108; 935/110; 530/323; 530/387; 530/806; 424/1.1
[58] Field of Search .................. 260/112 R, 112.5; 424/1.1, 9, 85, 87, 177; 436/518, 536–542, 547, 548, 804, 815, 825; 435/4, 7, 68, 70, 172, 240, 948, 885; 128/1.1, 659; 935/95, 99, 100, 102, 103, 104, 106–108, 110

[56] References Cited

U.S. PATENT DOCUMENTS 4,350,683  9/1982  Galfre .................. 424/85
4,381,292  4/1983  Bieber .................. 424/1.1
4,487,829 12/1984  Sharp .................. 435/7

OTHER PUBLICATIONS

Hill, H. R. et al, J. Exp. Med., vol. 159, pp. 1618–1628 (6–1984).
Komisar, J. L. et al in Host Defenses to Intracellular Pathogens, Plenum Press, N.Y. (1983), Eisenstein et al ed., pp. 303–311.
Muller, C. E. et al., J. Immunology, vol. 131(2), pp. 877–881 (8–1983).
Sanchez-Madrid, F. et al, J. Immunology, vol. 130(1), pp. 309–312 (1–1983).
Goding, J. W., Monoclonal Antibodies: Principles and Practice, Academic Press, N.Y. (1983), pp. 61–97.
Chiorazzi, N. et al, J. Exp. Med., vol. 156, pp. 930–935 (9–1982).
Steinitz, M. et al, J. Immunology, vol. 132(2), pp. 877–882 (2–1984).
Salton, M. R. J. in The Target of Penicillin, R. Hakenbeck et al, eds., Walter de Gruyter, Berlin (1983), pp. 3–8.
Rogers, H. J., Bacterial Cell Structure, Van Nostrand Reinhold, U.K. (1983), pp. 11–12, 25–27.
Kandler, O., Zbl. Bakt. Hyg., I. Abt. Orig. C3, 149–160 (1982).
Aspinall, G. O., The Polysaccharides, Academic Press, N.Y. (1982), pp. 1–2.
De Macario, E. C. et al, Proc. Natl. Acad. Sci., USA, vol. 80 (20), pp. 6346–6350 (10–1983), Bio. Abst. 77078373.
De Macario, E. C. et al, Fed. Proc., vol. 41(3), #3281 (1982), Bio. Abst. 23013991.
De Macario, E. C. et al, J. Immunology, vol. 129(4), pp. 1670–1674 (1982), Bio. Abst. 76052116.
Bahr, G. M. et al, Molecular Immunology, vol. 20(7), pp. 745–752 (1983), Bio. Abst. 77067541.
Jackson, D. E. et al, Infection & Immunity, vol. 43(3), pp. 800–803 (1984), CA Abstrt. 100:137104q.
Jackson, D. E. et al, Abst. Annu. Meet. Am. Soc. Microbiol., vol. 83, Abst. K147, Bio. Abst. 26047238 K151 Bio. Abst. 26047241 (1983).
Jenkins, R. B. et al, Fed. Proc., vol. 40(6), pp. 1812, Abstract 1572 (1981).
Caterson, B. et al., Fed. Proc., vol. 40 (3 parts), p. 798, Abstract 3231 (1981).
Bumol, T. F. et al, Proc. Natl. Acad. Sci., USA, vol. 79, pp. 1245–1249 (2–1982).
Jenkins, R. B. et al, J. Biol. Chem., vol. 256(16), pp. 8279–8282 (1981).
Bahr, et al., "Monoclonal Antibodies to the Synthetic Adjuvant Muramyl Dipeptide: Characterization of the Specificity, 20 Molecular Immunology 745–552 (1983).
Nahm, et al., "Monoclonal Antibodies to Streptococcal Group A Carbohydrate", 129 The Journal of Immunology 1513–1518 (1983).
Schleifer, et al., "The Immunochemistry of Peptidoglycan", 43 Eur. J. Biochem., 509–519 (1974).
Zeiger, et al., "Antibody Levels to Bacterial Peptidoglycan in Human Sera During the Time Course of Endocarditis and Bacteremic Infections Caused by Staphyloccus aureus", 33 Infection and Immunity 795–800 (1981).
Ruch, et al., "Monoclonal Antibody to Streptococcal Group B Carbohydrate: Applications in Latex Agglutination and Immunoprecipitin Assays, 16 Journal of Clinical Microbiology 145–152 (1982).
Rolicka, et al., "Antimucopeptide Antibodies and Their Specificity", 103 The Journal of Immunology 196–203 (1969).

Primary Examiner—Thomas G. Wiseman
Assistant Examiner—M. Moskowitz
Attorney, Agent, or Firm—Seidel, Gonda, Goldhammer & Abbott

[57] ABSTRACT

Several novel hybridoma cell lines, ATCC #HB-8510, 8511, 8512, 8513, 8514, 8515, 8516, and 8517 produce monoclonal antibody to an antigen, peptidoglycan, which is a normal structural component of nearly all true bacteria. Each antibody reacts not only with peptidoglycan from the immunizing bacterial strain but also peptidoglycan from other strains. Certain of the members of the hybridoma panel produce monoclonal antibody which reacts with peptidoglycan from substantially any peptidoglycan-possessing bacterium. The hybridomas are formed by fusing spleen cells from immunized Balb/c mice with SP2/O-Ag14 myeloma cells. Diagnostic and therapeutic uses of the monoclonal antibodies are provided.

31 Claims, No Drawings

MONOCLONAL ANTIBODIES TO PEPTIDOGLYCAN AND METHODS OF PREPARING SAME

REFERENCE TO GOVERNMENT

The invention described herein was supported by National Institutes of Health grants DE-03487 and DE-05160.

FIELD OF THE INVENTION

This invention relates to new hybrid cell lines for production of monoclonal antibody to peptidoglycan antigen. The antigen is found on nearly all bacteria, including the major bacterial pathogens of man and animals. This invention relates to the hybrid cell lines, the antibody so produced, and to diagnostic and therapeutic methods and compositions using these antibodies.

BACKGROUND OF THE INVENTION

The fusion of mouse myeloma cells to spleen cells was demonstrated by Kohler and Milstein (Nature 256, 495-497, 1975) allowing the generation of continuous cell lines making homogeneous (so-called "monoclonal") antibody. Subsequently, much effort has been directed toward the production of various hybrid cells (called hybridomas) and to uses of antibodies made by these hybrid cells. While the general technique is well understood conceptually, difficulties may be encountered in individual cases. Thus, the technique must be varied to meet the requirements of each specific case. There is no assurance, prior to attempting to prepare a given hybridoma, that the desired hybridoma will be obtained. There is no assurance that it will produce antibody, or that the antibody so produced will have the desired specificity.

Few instances of production of monoclonal antibody to bacterial antigens have been reported. The reported hybridomas produce antibody to non-peptidoglycan antigens unique to a single bacterial genus, species, type or strain, not to common antigens shared by all or nearly all bacteria. Ruch, F. E., Jr. and L. Smith, J.Clin.Microbiol. 16, 145-152 (1982); Nahm, M. H., B. L. Clevinger and J. M. Davie, J.Immunol. 129, 1513-1518 (1982).

Polyclonal antisera to peptidoglycan have been reported. Zeiger, A. R., C. V. Tuazon, and J. N. Sheagren, Inf.&Imm. 33, 795-800 (1981); Schleifer, K. H., and P. H. Seidl, Eur.J.Biochem. 43, 509-519 (1974); Rolicka, M. and J. T. Park, J.Immunol. 103, 196-203 (1969).

True bacteria, referred to as Eubacteria, are considered to be among the group of microorganisms called prokaryotes. Basically, prokaryotes are organisms of small overall dimensions that possess a relatively simple and primitive cellular structure. Unlike eukaryotic cells (which include mammalian cells, algae, fungi, and protozoa), prokaryotic cells lack a nuclear membrane so that the single circular prokaryote chromosome is bathed in cytoplasm. Prokaryotic cells also lack true intracellular organelles such as mitochondria and lysosomes which are enclosed by membranes.

In addition to Eubacteria, prokaryotes include a group of organisms called Archaebacteria (primitive bacteria). Kandler, O., Zbl.Bakt.Hyg., I.Abt.Orig. C 3, 149-160 (1982). This last group does not contain any organisms of known importance to human disease. It includes some extreme halophiles and thermoacidophiles that can be clearly distinquished from bacteria by differences in the structure of their cell surface.

Eubacteria include Mycoplasmatales, which differ from other prokaryotic cells in their lack of a peptidoglycan-containing cell wall. "Peptidoglycan" is also known as "murein" or "mucopeptide."

In the absense of any stain, Eubacteria are very difficult to see under a light microscope. The most commonly used stain, the gram stain, divides Eubacteria into two structurally, chemically, physiologically and medically important groups. "Gram-positive" species retain primary stain (crystal violet), after treatment with a mordant (iodine) and a decolorization procedure using ethanol or acetone. They have a relatively thick, polysaccharide-containing cell wall. "Gram-negative" species lose the primary stain-iodine complex during the decolorizing step. So that all cells are easily visible, a pink-colored counterstain is used. They possess a cell wall containing a large amount of lipid, particularly in the portion of the cell wall commonly called the "outer membrane".

It is understood that all Eubacteria (true bacteria) with the exception of the Mycoplasmatales, i.e. mycroplasma and acholeplasma, have been shown to possess peptidoglycan, a unique cell wall polymer that contains a novel amino sugar in its structure, muramic acid. The peptidoglycan polymer is essential for the growth and survival of bacteria in most environments, and peptidoglycan assembly on the exterior of the cytoplasmic membrane can be selectively interrupted by the appropriate application of certain chemotherapeutic agents.

Peptidoglycan is not present in eukaryotic cells. Such cells include mammalian, plant, protozoan and fungal cells. Peptidoglycan is not present in Archaebacteria or viruses.

Eubacteria, contain the major bacterial pathogens of man and animals. Eubacteria include the following genera: Escherichia, Pseudomonas, Proteus, Micrococcus, Acinetobacter, Klebsiella, Legionella, Neisseria, Bordetella, Vibrio, Staphylococcus, Lactobaccilus, Streptococcus, Bacillus, Corynebacteria, Mycobacteria, Clostridium, and others. Kandler, O., Zbl. Bakt.Hyg., I.Abt.Orig. C3, 149-160 (1982).

Peptidoglycan consists of glycan chains composed of N-acetylglucosamine and N-acetylmuramic acid linked by $\beta$-1-4-glycosidic bonds. Muramic acid is a nine-carbon amino sugar that is present only in Eubacteria and can be considered to be N-acetylglucosamine with a lactyl side chain on carbon 3. The peptide side chains of peptidoglycans are covalently (amide) linked to the carboxyl of the lactyl moiety of the muramic acid residues. A unique feature of this macromolecule that contributes to its insolubility, strength, and probably also its shape, lies in the peptide bond between the peptide side chains, resulting in a cross-linked, two- or three-dimensional structure. These peptide cross-links differentiate peptidoglycan from cellulose of plants and chitin of fungi and crustaceans.

A further peculiarity of bacterial cell wall peptidoglycans lies in the chemistry of the peptide side chains. Common features and differences in amino acid composition of these peptides can be illustrated as follows: The amino acid amide linked to N-acetylmuramic acid is almost always L-alanine. The second amino acid in the sequence is usually a D-amino acid, most frequently D-glutamate (or D-glutamine). The third amino acid is linked to this D-amino acid, not to the conventional α-carboxyl group found in proteins but to the other (γ) carboxyl group, resulting in the presence of the entire carbon skeleton of the second amino acid in the chain. This third amino acid is usually an L-(di)amino acid such as L-lysine or mesodiaminopimelic acid (DAP). DAP is another compound found only in eubacterial cells. When examined, it is the L-isomeric center of DAP (or other diamino acid) that is peptide linked to the second amino acid. The fourth amino acid is almost always D-alanine. Thus, the usual peptide side chain has an L-D-L-D sequence, different from the all L-amino acid sequence of proteins, and resistant to most proteinases, including the enzymes present in the digestive tract.

Cross-linking of the peptide side chains occurs usually between the second amino group of the diamino acid in position 3 of a peptide on one glycan strand and the carboxyl group of terminal D-alanine on a second glycan strand. In some species, this is a direct linkage from the ε-amino group of DAP or L-lysine to the carboxyl of D-alanine. In other species, one or more amino acids may be present in the bridge between the ε-amino group of L-lysine and D-alanine.

The chemical composition and structure of the peptidoglycan of an individual bacterial species is known to remain constant under a variety of environmental conditions. Ghuysen, J. M. and G. D. Shockman in *Bacterial Membranes and Walls*, pp. 37–130 (1973); Rogers, H. J. et al., *Microbial Cell Walls and Membranes* (1980). This consistency has led to the suggestion that peptidoglycan composition and chemical structure is useful for taxonomy. Kandler, O., Zbl. Bakt.Hyg., I.Abt.Orig. C 3, 149–160 (1982); Schleifen, K. H. and Kandler, O., *Bacteriol. Rev.* 36, 407–477 (1972).

Common features of peptidoglycan chemistry are believed responsible for the cross-reactivity of single monoclonal antibodies of the present invention to peptidoglycans from widely different bacterial species. Differences in peptidoglycan chemistry are believed responsible for the more limited cross-reactivity of other monoclonal antibodies of the present invention which react significantly with peptidoglycans from only some bacterial species.

The importance of rapid detection of bacterial pathogens in clinical specimens (from the blood, tissues, and body spaces and cavities) is well-recognized. The standard method for determining the presence of bacteria comprises placement of the subject specimen in a medium which will support the growth of bacteria. Growth is detected by a variety of methods including direct observation, detection of nutrient utilization and detection of bacterial metabolic products. Since culture methods require a substantial time period for bacterial growth, implementation of appropriate antimicrobic therapy is delayed.

In normally sterile specimens such as blood and cerebrospinal fluid, the presence of bacteria indicates a potentially life threatening situation and dictates an immediate course of antobiotic therapy. The need for more rapid detection methods has given rise to a number of antibody-based detection methodologies. These methodologies employ antibodies from sera or from hybridoma cell lines which detect individual bacterial species or strains, but which lack the broad specificities of the monoclonal antibodies of the present invention. Appropriate diagnosis of bacterial infection or contamination depends on the ability to detect all bacteria.

DEFINITIONS

As used hereinafter, "peptidoglycan-possessing bacteria" shall mean bacteria having a cell wall containing a form of peptidoglycan.

SUMMARY OF THE INVENTION

According to the present invention, eight novel hybridomas have been discovered providing cell lines producing novel monoclonal antibodies reacting with peptidoglycan. Some of these cell lines produce monoclonal antibody reacting with peptidoglycan from substantially any peptidoglycan-possessing bacterium. The remaining members of the hybridoma panel produce monoclonal antibody reacting with a large fraction of, but not all, peptidoglycan-possessing bacteria. Each hybridoma comprises a fused cell hybrid of a mouse spleen cell fused to a mouse myeloma. The donor mouse is previously immunized with cell wall material from a peptidoglycan-possessing bacterium. The hybridomas are, respectively, ATCC #HB-8510 through #HB-8517. Each antibody so produced is monospecific for a single determinant on peptidoglycan. The present monoclonal antibodies are not contaminated with other antibacterial immunoglobulins in contrast to prior art antisera which are not monospecific and which are inherently contaminated with antibody to numerous nonpeptidoglycan bacterial antigens. The present monoclonal antibodies are distinguished from prior art monoclonal antibodies which are bacterial group- or type-specific and which fail to possess the broad reactivity of the present monoclonal antibodies. The hybridomas of the present invention can be cultured to produce antibodies, without the necessity of immunizing and sacrificing animals followed by the adsorption and purification steps required to produce antisera of the prior art.

The hybridoma cell lines of the present invention are prepared by first immunizing mice with peptidoglycan-containing bacteria or fractions of such bacteria containing cell wall material. The spleen cells are then removed and a suspension thereof is made. The spleen cells are fused with mouse myeloma cells in the presence of a fusion promotor. The fused cells are diluted and cultured in separate wells in a medium which will not support the unfused myeloma or spleen cells. The supernatant in each well is evaluated for the presence of antibody to peptidoglycan. Hybridomas producing antibody reacting with peptidoglycan are selected and cloned. The antibody is recovered from the supernatant of the clone. The antibody reacts with the immunizing peptidoglycan fraction and to peptidoglycans isolated from other bacteria, both gram negative and gram positive.

Alternatively, the clones are transferred intraperitoneally into mice, and the resulting malignant ascites and serum containing the desired antibody is harvested.

A diagnostic method for detecting the presence of peptidoglycan-possessing bacteria comprises contacting a specimen with the monoclonal antibodies of the present invention, and detecting the material bound by the antibodies by immunological assay.

It is, accordingly, one object of this invention to provide hybridomas which produce antibodies against an antigen, peptidoglycan, found on nearly all bacteria.

Another object of this invention is to provide essentially homogeneous antibody against this antigen.

It is another object of this invention to provide homogeneous antibody which reacts with peptidoglycan from two or more diverse bacteria.

Another object of this invention is to provide homogeneous antibody reacting with substantially any peptidoglycan-possessing bacterium.

A still further object of this invention is to provide methods for detection of bacteria, and the diagnosis or treatment of bacterial disease using monoclonal antibodies directed against peptidoglycan.

Other objects and advantages of the invention will become apparent from the examination of the present disclosure.

DETAILED DESCRIPTION OF THE INVENTION

The method of preparing the hybridomas of the present invention generally comprises the following steps: Immunogen is prepared by extraction of intact cells of *Streptococcus mutans* with hot trichloroacetic acid. the insoluble residue resulting from this treatment is used as the immunogen for preparing the hybridomas described below. The extract was not re-acylated after extraction but it is believed that re-acylation would also provide a suitable immunogen. Other strains or species of peptidoglycan-possessing bacteria may be used as a source of immunogen. Other suitable methods for preparation of insoluble peptodoglycan may be used, e.g., treatment with hydrochloric acid or other acids, extraction with hot sodium dodecylsulfate, etc. Still other methods are readily available from the literature.

Mice are immunized with bacterial peptidoglycan. Male or female BALB/cJ mice are preferred, although other strains of mice may be used. The regimen for immunization and dosage of peptidoglycan should be such as to produce significant levels of specific serum antibodies. A combination of one dose in Incomplete Freunds Adjuvant given both intraperitoneally and subcutaneously, followed by intraperitoneal injections in saline (e.g., 25 μg peptidoglycan/0.2 ml/mouse) at 1- to 2-week intervals, was found effective. An additional intraveneous dose 3–4 days prior to fusion was found to provide useful numbers of suitably primes splenocytes.

Upon completion of the immunization regimen, the mice are sacrificed and their spleens removed. A suspension of splenocytes in a suitable medium is prepared. Approximately 5 ml of medium per spleen is sufficient. The protocols for in vitro cell suspension are well established. Kennett, R. H., "Fusion Protocols," in *Monoclonal Antibodies* (Kennett R. H., McKearn T. J., and Bechtol K. B. eds.), Plenum Press, New York and London, 365–367 (1980).

The suspended spleen cells are fused with a suspension of mouse myeloma cells by a fusion promoter. The preferred ratio is approximately 4 spleen cells per myeloma cell. A total volume of 1.0 ml of fusion medium is sufficient for $5 \times 10^7$ to $10^8$ splenocytes. The mouse myeloma cell line is preferably one of the "drug-resistant" type, to enable selection of hybrids. The most frequently used class of myelomas are the 8-azaguanine-resistant cell lines, which are widely known and available. These cell lines lack the enzyme hypoxanthine quanine phosphoribosyl transferase and therefore do not survive in HAT (hypoxanthine, aminopterin and thymidine) medium. Additionally, it is preferred that the myeloma cell line used does not itself produce any antibody, although in some circumstances, secreting myeloma lines may be preferred. While the preferred fusion promotor is polyethylene glycol of average molecular weight 1000 to 4000 (commercially available, e.g., as PEG 1000, J. T. Baker Chemical, Phillipsburg, N.J.), other known fusion promotors may be used.

A mixture of unfused myeloma cells, unfused spleen cells, and fused cells is distributed for culturing in separate compartments in a selective medium that will not support growth of unfused myeloma cells. Distribution of cells may be by a limiting dilution method, in which a certain number of cells are delivered in a known volume of medium into separate containers, such as wells in microtiter plates. McKearn T. J., "Cloning of Hybridoma Cells By Limiting Dilution in Fluid Phase" in *Monoclonal Antibodies,* p. 374. When HAT is used as the medium, unfused 8-azaguanine-resistant myeloma cells will not grow. Unfused spleen cells will normally die after about 7 days, since they are non-malignant. Culturing proceeds for a time sufficient to allow their death. Fused cells continue to reproduce and grow in the selective medium.

The supernatant in each container or compartment having hybrid cell growth is screened and evaluated for the presence of antibody to bacterial peptidoglycan. Hybridomas secreting the desired antibody are selected such as by limiting dilution, and cloned.

After selection and cloning, the desired hybridoma may be produced by either in vitro culturing or by in vivo peritoneal exudate (ascites) induction in mice. The first method will yield monoclonal antibody of higher purity. The desired hybridoma is cultured in a suitable medium for a suitable period of time (these parameters are known or easily determined). The desired antibody is recovered from the supernatant, essentially free of all other specific anti-peptidoglycan immune globulin. In medium containing serum (such as fetal calf serum), a small amount of other immune globulin is present.

If the in vitro technique does not produce a sufficient amount of antibody (usually a concentration of 25–50 μg/ml), then the desired hybridoma may be injected into the peritoneal cavity of syngeneic or semi-syngeneic mice. After a suitable period of incubation, the hybridoma will induce formation of antibody-secreting tumors, which will result in a higher concentration (5–20 mg/ml) of the desired antibody in the bloodstream and peritoneal exudate (ascites) of the injected mouse. The monoclonal antibody harvested from ascites or serum will be contaminated to about 5% with normal antibodies from the host mouse. However, these antibodies will generally not display specificity for bacterial peptidoglycan. If a myeloma cell line is used which secretes light chains, the concentration of monoclonal antibody obtained will be decreased without any effect on the antibody specificity.

The following is one typical prodedure for preparing a hybrid cell line of the present invention and is not intended to limit the same.

EXAMPLE I

Preparation of the Immunogen

*S. mutans* strain BHT (Coykendall, A. L., J.Gen.Microbiol. 83,327–338 (1974)) was cultured overnight in Todd-Hewitt broth (Difco Laboratories, Inc., Detroit, MI) and harvested by centrifugation. The pelleted bacteria were resuspended in hot 5% (v/v) trichloroacetic acid and held at 90° C. for 10 min. After centrifugation, the pellet was washed with 70% (v/v) ethanol in distilled water and then resuspended in Tris-HCl buffer, pH 8.0, containing 50 μg/ml trypsin (Sigma Chemical Co., St. Louis, Mo.). Following incubation at 37° C. for 2 hr, the material was washed five times with distilled water, and lyophilized.

EXAMPLE II

Production of Monoclonal Antibodies

A. Immunization and somatic cell hybridization

Male or female BALB/cJ mice (Jackson Laboratories, 8–10 weeks old) were immunized intraperitoneally with 50 μg S. mutans BHT peptidoglycan in 0.2 ml of Incomplete Freunds Adjuvant. Seven days later the mice were immunized with 25 μg peptidoglycan in saline subcutaneously and intraperitoneally. Ten days after this second injection they were immunized with 25 μg peptidoglycan in saline intraperitoneally. After a test bleed established the presence of high titers of specific antibodies in the sera of the mice, 25 μg of antigen was given intraveneously. Spleens were removed four days later, and single cell suspensions were made by teasing apart the spleens with forceps, followed by gentle pipetting of the cell clumps.

Cell fusion was carried out following the procedure of Kohler and Milstein, Nature 256, 495–497 (1975). Two $\times 10^8$ spleen cells were fused in 2 ml of fusion medium (40% PEG in Dulbecco's MEM [GIBCO, Grand Island, N.Y.]) with $5 \times 10^7$ SP2/0-Ag14 myeloma cells (Shulman, Nature 276, 269–270 (1978)), supplied by Dr. J. Cebra, University of Pennsylvania. These myeloma cells do not secrete heavy or light immunoglobulin chains.

B. Selection and growth of hybridomas

After cell fusion, cells were cultured in HAT medium (hypoxanthine, aminopterin and thymidine) at 37° C. with 10% $CO_2$ in a humid atmosphere. Ten to twenty-one days later 50 μl of supernatant from hybridoma-containing cultures were added to microtiter wells containing 50 μl of peptidoglycan suspension (0.1–0.5 ng/ml). Detection of mouse hybridoma antibody binding to S. mutans BHT peptidoglycan was accomplished by enzyme-linked immunosorbent assay (ELISA). After reaction of peptidoglycan with supernatants, the peptidoglycan pellets were reacted with horseradish peroxidase-labeled goat anti-mouse antibody (Kirkegaard and Perry Labs, Inc., Gaithersburg, Md., hereinafter "KPL") and the presence of enzyme-conjugated antibody disclosed with a suitable chromagen. Hybridoma cultures containing antibody activity specific for peptidoglycan were selected and cloned by a limiting dilution technique. McKearn, T. J., "Cloning of Hybridoma Cells, etc." in Monoclonal Antibodies, p. 374. Subsequently, these clones were injected intraperitoneally (approximately $2 \times 10^7$ cells in 0.5 ml/mouse) into BALB/cJ mice that had been primed 10–14 days previously with 0.5 ml pristane (2,6,10,14-tetramethylpentadecane; Aldrich Chemical Company, Milwaukee, Wis.). The tumor-induced ascites fluid was harvested from the mice and used to investigate reactivity of the antibodies with peptidoglycans from various bacteria and peptidoglycan-related compounds, as described below in Example III.

EXAMPLE III

Characterization of Hybrid Antibody Reactivities

A. Subclass and specificity analyses

By standard enzyme-linked immunosorbent assary (ELISA) methods, (Gerhard, W. et al., "Monoclonal Antibodies Against Influenza Virus" in Monoclonal Antidoies, p. 331), the subject hybridomas were demonstrated to be of the antibody subclasses (isotypes) shown in Table 1. Potential inhibitors were serially diluted in phosphate-buffered saline and incubated with predetermined amounts of hybridoma antibodies, such amounts being required to give a positive ELISA result. After 1 hr incubation at room temperature, samples were reacted with S. mutans BHT peptidoglycan in the standard assay. The compounds tested in this manner which failed to inhibit reactivity with the antigen were: 10 mM muramyldipeptide (N-acetylmuramyl-L-alanine-D-isoglutamine or "MDP"), 100 mM N-acetylglucosamine, 8 mg/ml acid-hydrolyzed chitin (oligomers of N-acetylglucosamine), and 2 mg/ml insoluble chitin (polymer of N-acetylglucosamine).

TABLE 1

| Clone | ATCC No. | Antibody Isotype |
|-------|----------|------------------|
| 4D3   | HB-8517  | IgM, κ           |
| 3G3   | HB-8516  | IgM, λ           |
| 14C2  | HB-8515  | IgM, κ           |
| 3E9   | HB-8514  | IgM, κ           |
| 10E5  | HB-8513  | IgM, κ           |
| 3F6   | HB-8512  | IgM, κ           |
| 3C11  | HB-8511  | $IgG_1$, κ       |
| 15B2  | HB-8510  | $IgG_3$, κ       |

B. Isolation of Cell Wall Peptidoglycan Antigens

Cell wall peptidoglycan was isolated from Streptococcus, Staphylococcus and Bacillus species by trichloroacetic acid treatment as follows. Bacteria were harvested from overnight cultures (2 liters) by centrifugation. Pellets were resuspended in 10 ml hot 5% (v/v) trichloroacetic acid and held at 90° C. for 10 min. After centrifugation, pellets were washed with 30 ml 70% (v/v) ethanol, 30 ml distilled $H_2O$ and finally resuspended in 5 ml 50 mM Tris-HCl, (tris(hydroxymethyl)aminomethane-HCl), pH 8.0, containing 50 μg/ml trypsin. Following 2 hr incubation at 37° C., the insoluble material was washed five times with $H_2O$ and lyophilized.

Cell wall peptidoglycan was isolated from Escherichia coli and Pseudomonas aeruginosa by sodium dodecylsulfate (SDS) treatment as follows. Bacteria were harvested from overnight cultures (2 liters) by centrifugation. Pellets were extracted with 5% (v/v) SDS at 90° C. for 3 hr., then left stirring overnight at room temperature. The insoluble material was pelleted by centrifugation and washed to remove detergent (once with water, once with acetone, and five times with water). After resuspension in 50 mM Tris-HCl, pH 8.0, containing 10 μg/ml trypsin, and incubation for 2 hr at 37° C., the insoluble material was washed five times with water and lyophilized.

C. Analysis of reactivities by immunoassay

Analysis of reactivity of hybridomas against all preparations of peptidoglycans (from part B. of this Example) was performed by ELISA techniques. Peptidoglycans were allowed to adhere to polystyrene microtiter plates (Falcon, Oxnard, CA) at approximately 10 μg/50 μl/well in 50 mM carbonate, pH 9.6, for 18 hr at 4° C. Serial dilutions of ascites or supernatant samples containing individual hybridomas were made in PBS (phosphate-buffered saline) and transferred to peptidoglycan-coated plates. After 1 hr incubation at room temperature, plates were washed five times in PBS containing 0.2% polyoxyethylene sorbitan monolaurate ("Tween 20", Sigma Chem. Co., St. Louis, Mo.) and a peroxidase-conjugated anti-mouse immunoglobulin (KPL) was added and incubated for 1 hr at room temperature. Following five washes with PBS-Tween 20, plates were developed by addition of peroxidase substrate ABTS (KPL) and results were read after 15 min.

known to contain mesodiaminopimelic acid in place of lysine found in *S. mutans* BHT. Peptidoglycan from *S. faecium* ATCC 9790 and *Staphylococcus epidermidis* contain D-isoasparagine and glycine respectively, two amino acids which are absent from *S. mutans* BHT peptidoglycan. Antibody from clones 15B2, 3C11 and 3F6 reacted strongly with antigen from all six bacterial strains, despite these significant variations in peptidoglycan chemistry. Monoclonal antibody from clones 15b2 and 3F6 will detect substantially any peptidoglycan-possessing bacteria. They may be used to differentiate between the presence of bacteria and other microbial forms such as fungi, protozoa or viruses.

The remaining members of the hybridoma panel pro-

TABLE 2

| | Reactivity (Log$_2$ ELISA titer) with insoluble peptidoglycan from: | | | | | |
|---|---|---|---|---|---|---|
| | Gram Positive | | | | Gram Negative | |
| Clone | *Streptococcus mutans* BHT | *Streptococcus faecium* 9790 | *Staphylococcus epidermidis* | *Bacillus subtilis* | *Escherichia coli* | *Pseudomonas aeruginosa* |
| 4D3 | 19.0 | 8.6 | 12.6 | 12.6 | 11.0 | 12.0 |
| 3G3 | 12.0 | 11.3 | 7.3 | 8.3 | 5.3 | 4.3 |
| 14C2 | 19.0 | 16.6 | 10.3 | 13.6 | 16.0 | 17.0 |
| 3E9 | 18.0 | 10.6 | 13.0 | 13.0 | 14.0 | 15.0 |
| 10E5 | 18.0 | 15.6 | 13.0 | 13.0 | 15.0 | 15.0 |
| 3F6 | 16.0 | 15.6 | 13.0 | 14.0 | 15.0 | 14.0 |
| 3C11 | 13.6 | 10.6 | 10.6 | 11.6 | 10.6 | 10.6 |
| 15B2 | 11.0 | 10.6 | 10.6 | 11.6 | 9.6 | 10.6 |

DISCUSSION OF THE DATA

Results of studies to characterize the specificity and reactivity of antibody from each of eight hybridomas prepared according to the present invention are illustrated in Table 2. Hybridoma preparation, and production and characterization of monoclonal antibodies secreted therefrom, were performed as described in the above Examples. Large quantities of hybridomas were prepared by injecting individual subject hybridomas intraperitoneally into mice and harvesting the tumor-induced ascites. Smaller quantities of individual hybridoma antibodies were removed from supernatants following standard in vitro culture of hybridoma cells.

A sample of each subject hybridoma was deposited at the American Type Culture Collection, 12301 Parklawn Drive, Rockville, Md. 20852, on Feb. 29, 1984 and have been assigned the ATCC numbers set forth in Table I. Table I also shows the immunoglobulin isotypes of the subject monoclonal antibodies.

Referring to Table 2, each of the eight hybrid cell lines produces antibody reacting with immunogen at high titers, i.e., insoluble peptidoglycan from *S. mutans* strain BHT. Each antibody cross-reacts with peptidoglycans prepared from five other widely different bacterial genera and species. The six bacteria tested represent four different genera of Gram positive and two different genera of Gram negative bacteria. The extent of cross-reactivity varies for each monoclonal antibody of the panel.

Clones 15B2 (#HB-8510) and 3F6 (#HB-8512) produce antibody reacting with peptidoglycans prepared from each of the six widely different bacteria, at titers virtually indistinguishable from those observed with the immunogen, *S. mutans* BHT peptidoglycan. These strong reactions occurred even though the subject bacterial peptidoglyans are known to differ markedly in chemical structure from the peptidoglycan of *S. mutans* BHT. Peptidoglycan from the two Gram negative species, *Escherichia coli* and *Pseudomonas aeruginosa*, and from the Gram positive species *Bacillus subtilis*, are duce selective antibodies reacting with some, but not all, of the heterologous peptidoglycans at high titers. Thus, these monoclonal antibodies can be used singly or in combination to detect peptidoglycan from a range of Eubacteria. Antibody from clone 3E9 (#HB-8514) reacted strongly with all bacterial peptidoglycans tested except for *Streptococcus faecium* ATCC 9790. Antibody from clone 3G3 (#HB- 8516) reacts at high titer with peptidoglyan of *S. faecium* ATCC 9790, but at lower titer with the remaining bacterial peptidoglycans tested.

Compounds that are structurally related to portions of the peptidoglycan immunogen fail to be recognized by any of the subject monoclonal antibodies. N-acetylglucosamine alone, although one of the constituent amino sugars of the peptidoglycan backbone, does not inhibit reactivity of the hybridomas with *S. mutans* peptidoglycan at 100 mM concentration. Chitin (polymer of N-acetylglucosamine) and acid-hydrolyzed chitin (oligomers of N-acetylglocosamine) were similarly ineffective as inhibitors. Muramyldipeptide (MDP) represents the minimal fragment of peptidoglycan capable of mimicing the in vitro and in vivo adjuvant properties of peptidoglycan. However, at 10 mM concentration, this molecule was unable to interfere in the reaction between any of the subject monoclonal antibodies and *S. mutans* peptidoglycan.

The preparation of the hybridomas and the production and characterization of the resultant monoclonal antibodies may be performed as in the above examples. While large quantities of the subject antibodies have been prepared by injecting the subject hybridoma intraperitoneally into mice and harvesting ascites or blood, it is clearly understood that the hybridomas can be cultured in vitro by techniques described in the art, and the antibody removed from the culture supernatant.

The present invention provides a panel of hybridomas capable of producing monoclonal antibodies against peptidoglycan, an antigen found on nearly all bacteria. All true bacteria (Eubacteria), except for the families mycoplasma and acholeplasma, are known to contain peptidoglycan. It is noted that within the peptidoglycan-possessing genera are the major bacterial pathogens of man and animals.

Although a panel of eight hybridoma producing monoclonal antibodies against peptidoglycan is described, it is contemplated that the present invention encompasses all monoclonal antibodies exhibiting the characteristics described herein. The hybridomas of the panel belong to one of the following subclasses IgM, $IgG_1$, or $IgG_3$ (Table I). These subclasses of immune globulin (Ig) differ from one another in the so-called "constant" regions, although an antibody to a specific antigen will have a so-called "variable" region which functionally recognizes the antigen regardless of which subclass of immune globulin to which it belongs. This means that a monoclonal antibody exhibiting the characteristics described herein may be of subclasses IgG, $IgG_{2a}$, $IgG_{2b}$, $Ig_3$, IgM, IgA or other Ig classes. The difference among Ig's will not affect the reactivity pattern of the antibody toward antigen, but may affect the further reaction of the antibody with other materials, such as complement or anti-mouse antibodies. Although the panel of antibodies described herein belong to IgM, $IgG_1$, or IgG3 subclasses, it is contemplated that antibodies having the broad spectrum reactivity of the present panel are included within the subject invention regardless of the Ig class or subclass to which they belong.

Further included within the present invention are the methods for preparing monoclonal antibodies described here. It is contemplated that one skilled in the art could follow immunization, fusion, and selection methods provided herein and generate cell lines capable of producing antibodies against peptidoglycan. Since the individual hybridoma cannot be further identified except by reference to the antibody produced, it is contemplated that any hybridoma producing antibody to peptidoglycan is included within the subject invention, as are methods for making this antibody employing such hybridoma.

Although the hybridomas described herein are formed from cells of murine origin, it is contemplated that one skilled in the art could follow the methods provided to form hybridomas providing antibody to peptidoglycan by fusing myelomas and splenocytes from other vertebrates.

Although the monoclonal antibodies described herein are produced by hybridomas, it is contemplated that other methods may be used to produce monoclonal antibodies reacting with peptidoglycans, for example, any method that would cause an antibody-producing cell to become immortal. Such methods include transformation via the insertion of DNA either directly or through a viral vector (Larrick, J. W. and, D. W. Buck, Biotechniques 2, 6–14 (1984)).

The monoclonal antibodies of the present invention have application to diagnosis and treatment of bacterial disease. These techniques may be employed using a single monoclonal antibody alone or in combination with other monoclonal antibodies of the present invention specific to peptidoglycan.

Cell wall antigens, including peptidoglycans, are often immunologically masked by other cell surface materials. qIn Gram positive bacteria, peptidoglyan may be masked by other polysaccharides or proteins. In Gram negative bacteria, it may be masked by the cell outer membrane. Unmasking is easily achieved by chemical methods. Typical of these methods is acid treatment. Park, J. T. and R. Hancock, J.Gen.Microbiol., 22, 249 (1960). Unmasking may also be achieved with cell wall hydrolytic enzymes. Ghuysen, J. M., Bacteriol.Rev. 32, 425–64 (1968). A number of commercially available diagnostic test kits use unmasking methods on intact bacteria to permit the antibodies in these kits to recognize cells. Such tests are sold under the trademark or tradenames "Streptex" (Wellcome Reagent Ltd., Beckenham, England; enzymatic), "Direction Group A Strep Test" (Hynson, Westcoff and Dunning, Baltimore, Md.; enzymatic), and "Culturette Group A Strep ID" (Marion Scientific, Kansas City, Mo.; acid treatment).

For testing some bacterial specimens, it may be unnecessary to unmask peptidoglycan. Certain bacteria contain peptidoglycan exposed at the cell surface. Schleifer, K. H. and R. M. Krause, J.Biol.Chem., 246, p. 986–94 (1971). In addition, it is known that many intact bacteria shed or secrete cell wall antigens, including peptidoglycan, during cell growth or death. Rogers et al., *Microbial Cell Walls and Membranes*, p. 564. Thus, unmasked peptidoglycan may be available in many bacteria-containing specimens allowing the antibodies of the present invention to recognize peptidoglycan-containing bacterial fragments or intact bacteria without prior chemical or enzymatic treatment to unmask peptidoglycan.

The monoclonal antibodies of the present invention are useful in detecting the presence of bacteria in specimens of interest by means of standard immunological detection methods including, but not limited to, radioimmunoassay, ELISA, fluorescent assay, precipitation, agglutination, and antigen capture. The body fluid or other specimen of the patient in question is treated to expose the peptidoglycan (if not already exposed) and contacted with antibody. The material bound thereto measured. By appropriate labelling with radioactive materials, heavy metals, and other labelling means, the antibodies provide a specific means of in vivo imaging of bacteria-caused infectious disease processes.

The monoclonal antibodies of the present invention are useful in removing peptidoglycan-containing materials from fluids thereby providing a method of therapy for bacteria-mediated disease as well as a method for decontaminating body fluids, foods and industrial products. Fluids are passed over an insoluble matrix to which antibody is attached. The antibody selectively removes substances containing peptidoglycan, namely intact bacterial cells, peptidoglycan-containing cell fragments and free peptidoglycan. Following removal of these contaminants, the blood or other bodily fluid may be returned to the body. The same procedure may be used to remove peptidoglycan-containing contaminants from other materials such as foods, pharmaceutical products and other substances wherein the presence of bacteria or bacterial cell wall fragments is undesirable.

It has been shown that peptidoglyans are responsible for numerous biological and immunological consequences of bacterial infection in mammalian hosts: pyrogenicity, mitogenicity, localized Shwartzman reaction, hypersensitivity, anticomplementary activity, antitumor activity and adjuvant activity. Shockman, G. D., R. Kessler, J. B. Cornett and M. Mychajlonka in *Secretory Immunity and Infection* (ed. J. R. McGhee, et al.) Plenum Pub. Corp., p. 803 (1978). The monoclonal antibodies of the present invention provide a means to bind, remove or concentrate peptidoglycans and peptidoglycan fragments responsible for these consequences.

It is contemplated that the monoclonal antibodies of the present invention, alone or in a combination with other molecules, can be used in vivo, for therapeutic purposes. Such compositions can be injected into the body to inactivate peptidoglycan-possessing bacteria.

The present invention may be embodied in other specific forms without departing from the spirit or essential attributes thereof and, accordingly, reference should be made to the appended claims, rather than to the foregoing specification, as indicating the scope of the invention.

What is claimed is:

1. A monoclonal antibody of class IgG or IgM which specifically binds to an antigenic determinant of eubacterial peptidoglycan.

2. A monoclonal antibody according to claim 1 produced by a hybridoma formed by fusion of cells from a myeloma line with spleen cells from a donor previously immunized with cell wall material from a species of Eubacteria.

3. A monoclonal antibody according to claim 1 which binds to peptidoglycan from substantially any species of Eubacteria.

4. A monoclonal antibody acording to claim 1 which is selected from the group consisting of the following subclasses: IgM, $IgG_1$, and $IgG_3$.

5. A monoclonal antibody according to claim 2 wherein the myeloma line and spleen cells are murine.

6. A monoclonal antibody according to claim 5 wherein the hybridoma is formed by fusion of SP2/0-Ag14 myeloma cells with spleen cells from a BALB/c mouse previously immunized by cell wall material from a species of Eubacteria.

7. Monoclonal antibody of class IgG or IgM which specifically binds to an antigenic determinant of peptidoglycan from two or more species of Eubacteria, produced by the method comprising the steps of:
   (a) immunizing a donor with a species of Eubacteria or fractions thereof containing cell wall material;
   (b) removing the spleens from said donor and making a suspension of said spleen cells;
   (c) fusing said spleen cells with donor myeloma cells;
   (d) diluting and culturing the fused cells in separate wells in a medium which will not support the unfused myeloma cells;
   (e) assaying the supernate in each well containing a hydridoma for the presence of antibody to peptidoglycan;
   (f) selecting and cloning a hybridoma producing antibody which reacts with peptidoglycan from two or more species of Eubacteria.

8. A monoclonal antibody according to claim 7 wherein the donor and the myeloma cells are murine.

9. A monoclonal antibody according to claim 8 wherein the method comprises the further steps of transferring said clones into mice and harvesting the malignant ascites or serum from said mice, said ascites or serum containing the desired antibody.

10. A monoclonal antibody according to claim 8 wherein the method comprises the further steps of culturing the hybridoma in a suitable medium and recovering the antibody from the supernatant above said hybridoma.

11. A method for producing a monoclonal antibody which specifically binds to an antigenic determinant of peptidoglycan comprising culturing a hybridoma selected from the group consisting of eight hybridomas numbered consecutively from ATCC #HB-8510 through ATCC #HB-8517 and recovering the secreted monoclonal antibodies from the culture medium.

12. A monoclonal antibody prepared according to the method of claim 11.

13. A method for producing a monoclonal antibody which specifically binds to an antigenic determinant of peptidoglycan comprising injecting into a mouse a hybridoma selected from the group consisting of eight hybridomas numbered consecutively from ATCC #HB-8510 through ATCC #HB-8517 and recovering the secreted monoclonal antibodies from the mouse ascitic fluid or serum.

14. A monoclonal antibody prepared according to the method of claim 13.

15. A composition comprising a continuous cell line which produces monoclonal antibody of class IgG or IgM which specifically binds to an antigenic determinant of eubacterial peptidoglycan comprising a cell hybrid formed from a mouse spleen cell previously immunized with peptidoglycan fused to a mouse myeloma, and a culture medium for said hybrid.

16. A composition according to claim 15 wherein the antibody binds to substantially any species of Eubacteria.

17. The composition according to claim 15 wherein the mouse spleen cell is from a BALB/c mouse.

18. The composition according to claim 15 wherein the mouse myeloma is SP2/0-Ag14.

19. A composition comprising a continuous cell line producing monoclonal antibody selected from the group of eight cell lines numbered consecutively from ATCC #HB-8510 through ATCC #HB-8517.

20. A diagnostic method for detecting the presence of Eubacteria, comprising contacting a specimen with monoclonal antibodies of class IgG or IgM which specifically bind to an antigenic determinant of eubacterial peptidoglycan, and detecting the material bound by said antibodies by immunological assay means.

21. A diagnostic method according to claim 20 wherein the monoclonal antibody binds to an antigenic determinant of eubacterial peptidoglycan from substantially any eubacterium.

22. A diagnostic method according to claim 20 wherein the specimen is fluid or tissue.

23. A diagnostic method according to claim 20 wherein the immunological assay means is selected from the group consisting of radioimmunoassay, enzyme-linked immunosorbent assay, fluorescent assay, precipitation, agglutination, and antigen capture.

24. A diagnostic method according to claim 20 additionally comprising the preliminary step of treating the specimen to unmask peptidoglycan.

25. A diagnostic method according to claim 24 wherein the preliminary step of treating the specimen to unmask peptidoglycan comprises treatment with acid.

26. A diagnostic method according to claim 24 wherein the preliminary step of treating the specimen to unmask peptidoglycan comprises enzymatic hydrolysis.

27. A method for removing peptidoglycan-containing materials from fluids comprising passing a fluid over monoclonal antibody of class IgG or IgM which specifically binds to an antigenic determinant of eubacterial peptidoglycan, said antibody being linked to an insoluble matrix, and binding said materials to said matrix-linked peptidoglycan.

28. A method according to claim 27 wherein the peptidoglycan-containing material comprises intact bacterial cells.

29. A method according to claim 27 wherein the peptidoglycan-containing material comprises peptidoglycan-containing cell fragments.

30. A method according to claim 27 wherein the peptidoglycan-containing material comprises free peptidoglycan.

31. A diagnostic method for detecting the presence of Eubacteria, comprising contacting a specimen with monoclonal antibody produced by a hybridoma selected from the group consisting of hybridomas numbered consecutively from ATCC #HB-8510 through ATCC #HB-8517 under conditions such that an immune-complex between said monoclonal antibody and any eubacterial peptidoglycan in said specimen is formed and detecting said immune complex as indicating the presence of Eubacteria.

* * * * *